(12) United States Patent
Raina et al.

(10) Patent No.: US 11,564,719 B2
(45) Date of Patent: Jan. 31, 2023

(54) DEVICES FOR MINIMALLY INVASIVE PROCEDURES

(71) Applicant: EDGE SURGICAL, INC., Chicago, IL (US)

(72) Inventors: Aniruddha Raina, Troy, MI (US); Robert F. Rioux, Ashland, MA (US); Christopher Wilson, Chicago, IL (US); Jim A. Youssef, Durango, CO (US)

(73) Assignee: EDGE SURGICAL, INC., Chicago, IL (US)

( * ) Notice: Subject to any disclaimer, the term of this patent is extended or adjusted under 35 U.S.C. 154(b) by 384 days.

(21) Appl. No.: 17/012,154

(22) Filed: Sep. 4, 2020

(65) Prior Publication Data

US 2020/0397487 A1 Dec. 24, 2020

Related U.S. Application Data

(62) Division of application No. 16/006,429, filed on Jun. 12, 2018, now Pat. No. 10,792,080.
(Continued)

(51) Int. Cl.
*A61B 17/70* (2006.01)
*A61B 5/107* (2006.01)
(Continued)

(52) U.S. Cl.
CPC ........ *A61B 17/7092* (2013.01); *A61B 5/1076* (2013.01); *A61B 5/6851* (2013.01);
(Continued)

(58) Field of Classification Search
CPC .......................... A61B 17/7092; A61B 5/1076
See application file for complete search history.

(56) References Cited

U.S. PATENT DOCUMENTS

| | | | |
|---|---|---|---|
| 1,987,504 | A | 1/1935 | Denz |
| 2,650,435 | A | 9/1953 | Kidd |
| 2,689,408 | A | 9/1954 | Cornell et al. |
| 3,058,225 | A | 10/1962 | Ward |
| 4,033,043 | A | 7/1977 | Cunningham |

(Continued)

FOREIGN PATENT DOCUMENTS

| | | |
|---|---|---|
| CN | 101137332 A | 3/2008 |
| CN | 205128995 U | 4/2016 |

(Continued)

OTHER PUBLICATIONS

European Search Report issued in European Application No. 19764582. 3, dated Jul. 20, 2021, 8 pages.

(Continued)

*Primary Examiner* — Andrew Yang
(74) *Attorney, Agent, or Firm* — Brown Rudnick LLP

(57) ABSTRACT

The invention relates to an assembly for use in minimally invasive surgical procedures, including bone implant fixation procedures. The assembly is configured to provide a faster and more accurate measurement of depth of holes for placement of bone screws and fasteners. The assembly includes a guidewire having a deployable distal hook member configured to securely anchor into a desired position relative to a hole drilled in a bone and thereby provide an accurate datum for a measuring instrument for determining a depth of the hole for subsequent screw placement. The assembly further includes a surgical depth instrument to cooperatively function with the guidewire and obtain one or more measurements while operably coupled to the guidewire.

17 Claims, 12 Drawing Sheets

Engage Opening of Drilled Hole

Related U.S. Application Data

(60) Provisional application No. 62/519,845, filed on Jun. 14, 2017.

(51) Int. Cl.
   *A61B 5/00* (2006.01)
   *A61B 17/00* (2006.01)
   *A61B 17/88* (2006.01)
   *A61B 90/00* (2016.01)

(52) U.S. Cl.
   CPC ...... *A61B 5/6859* (2013.01); *A61B 17/00234* (2013.01); *A61B 17/8897* (2013.01); *A61B 90/06* (2016.02); *A61B 2017/00026* (2013.01); *A61B 2017/00115* (2013.01); *A61B 2017/00199* (2013.01); *A61B 2017/00221* (2013.01); *A61B 2017/00323* (2013.01); *A61B 2017/00986* (2013.01); *A61B 2090/036* (2016.02); *A61B 2090/062* (2016.02); *A61B 2505/05* (2013.01)

(56) References Cited

U.S. PATENT DOCUMENTS

| | | | |
|---|---|---|---|
| 5,013,318 A | 5/1991 | Spranza, III | |
| 5,037,426 A | 8/1991 | Goble et al. | |
| 5,062,748 A | 11/1991 | Kishida | |
| 5,098,435 A | 3/1992 | Stednitz et al. | |
| 5,758,433 A | 6/1998 | Alberts | |
| 5,772,661 A | 6/1998 | Michelson | |
| 5,860,973 A | 1/1999 | Michelson | |
| 5,928,243 A | 7/1999 | Guyer | |
| 6,235,028 B1 | 5/2001 | Brumfield et al. | |
| 6,428,542 B1 | 8/2002 | Michelson | |
| 6,466,817 B1 | 10/2002 | Kaula et al. | |
| 6,500,128 B2 | 12/2002 | Marino | |
| 6,530,929 B1 | 3/2003 | Justis et al. | |
| 6,592,586 B1 | 7/2003 | Michelson | |
| 6,796,985 B2 | 9/2004 | Bolger et al. | |
| 6,916,320 B2 | 7/2005 | Michelson | |
| 6,936,050 B2 | 8/2005 | Michelson | |
| 6,936,051 B2 | 8/2005 | Michelson | |
| 6,945,933 B2 | 9/2005 | Branch et al. | |
| 6,969,390 B2 | 11/2005 | Michelson | |
| 7,008,422 B2 | 3/2006 | Foley et al. | |
| 7,165,336 B2 | 1/2007 | Kim | |
| 7,177,677 B2 | 2/2007 | Kaula et al. | |
| 7,444,756 B2 | 11/2008 | Kim | |
| 7,493,703 B2 | 2/2009 | Kim et al. | |
| 7,522,953 B2 | 4/2009 | Kaula et al. | |
| 7,607,238 B2 | 10/2009 | Kim et al. | |
| 7,657,308 B2 | 2/2010 | Miles et al. | |
| 7,664,544 B2 | 2/2010 | Miles et al. | |
| 7,676,943 B2 | 3/2010 | Kim et al. | |
| 7,685,735 B2 | 3/2010 | Kim | |
| 7,730,629 B2 | 6/2010 | Kim | |
| 7,878,981 B2 | 2/2011 | Strother et al. | |
| 7,895,762 B2 | 3/2011 | Kim et al. | |
| 7,895,767 B2 | 3/2011 | Harshbarger et al. | |
| 7,896,815 B2 | 3/2011 | Thrope et al. | |
| 7,942,826 B1 | 5/2011 | Scholl et al. | |
| 7,963,927 B2 | 6/2011 | Kelleher et al. | |
| 7,991,463 B2 | 8/2011 | Kelleher et al. | |
| 8,050,769 B2 | 11/2011 | Gharib et al. | |
| 8,068,912 B2 | 11/2011 | Kaula et al. | |
| D652,921 S | 1/2012 | Miles et al. | |
| 8,147,421 B2 | 4/2012 | Farquhar et al. | |
| 8,172,768 B2 | 5/2012 | Strother et al. | |
| 8,221,427 B2 | 7/2012 | Roh | |
| D666,294 S | 8/2012 | Miles et al. | |
| 8,255,044 B2 | 8/2012 | Miles et al. | |
| 8,255,045 B2 | 8/2012 | Gharib et al. | |
| 8,442,621 B2 | 5/2013 | Gorek et al. | |
| 8,500,652 B2 | 8/2013 | Strother et al. | |
| 8,562,539 B2 | 10/2013 | Marino | |
| 8,568,317 B1 | 10/2013 | Gharib et al. | |
| 8,591,431 B2 | 11/2013 | Calancie et al. | |
| 8,641,638 B2 | 2/2014 | Kelleher et al. | |
| 8,958,869 B2 | 2/2015 | Kelleher et al. | |
| 8,989,866 B2 | 3/2015 | Gharib et al. | |
| 9,131,947 B2 | 9/2015 | Ferree | |
| 9,232,906 B2 | 1/2016 | Wolf, II | |
| 9,295,396 B2 | 3/2016 | Gharib et al. | |
| 9,392,953 B1 | 7/2016 | Gharib | |
| 9,681,880 B2 | 6/2017 | Neubardt et al. | |
| 9,700,228 B2 | 7/2017 | Gharib et al. | |
| 9,743,853 B2 | 8/2017 | Kelleher et al. | |
| 9,750,508 B1 | 9/2017 | Barnes et al. | |
| 9,757,072 B1 | 9/2017 | Urbalejo | |
| 9,801,668 B2 | 10/2017 | Ferree | |
| 9,848,861 B2 | 12/2017 | Miles et al. | |
| 9,931,077 B2 | 4/2018 | Kaula et al. | |
| 10,132,607 B2 | 11/2018 | Rioux et al. | |
| 10,151,570 B2 | 12/2018 | Jacobs et al. | |
| 10,578,415 B2 | 3/2020 | Rioux et al. | |
| 10,578,416 B2 | 3/2020 | Jacobs et al. | |
| 2002/0104230 A1 | 8/2002 | White | |
| 2003/0139662 A1 | 7/2003 | Seidman | |
| 2003/0233098 A1 | 12/2003 | Markworth | |
| 2004/0167533 A1 | 8/2004 | Wilson et al. | |
| 2005/0066535 A1 | 3/2005 | Rupp et al. | |
| 2005/0119660 A1 | 6/2005 | Bourlion et al. | |
| 2005/0261585 A1 | 11/2005 | Makin et al. | |
| 2006/0224161 A1 | 10/2006 | Bhattacharyya | |
| 2007/0088366 A1 | 4/2007 | Fernandez | |
| 2008/0092695 A1 | 4/2008 | Hernandez | |
| 2008/0104855 A1 | 5/2008 | Kim et al. | |
| 2008/0125637 A1 | 5/2008 | Geist et al. | |
| 2008/0262526 A1 | 10/2008 | Neubardt et al. | |
| 2008/0269631 A1 | 10/2008 | Denison et al. | |
| 2009/0005786 A1 | 1/2009 | Prien et al. | |
| 2009/0157088 A1 | 6/2009 | Mengato | |
| 2009/0163901 A1 | 6/2009 | Fisher et al. | |
| 2009/0221922 A1 | 9/2009 | Lee et al. | |
| 2009/0264940 A1 | 10/2009 | Beale et al. | |
| 2010/0099066 A1 | 4/2010 | Mire et al. | |
| 2010/0154238 A1 | 6/2010 | Harshbarger et al. | |
| 2010/0198227 A1 | 8/2010 | Kim et al. | |
| 2010/0256517 A1 | 10/2010 | Neubardt et al. | |
| 2011/0054346 A1 | 3/2011 | Hausman et al. | |
| 2011/0060238 A1 | 3/2011 | Hausman et al. | |
| 2011/0060243 A1 | 3/2011 | Hausman et al. | |
| 2011/0238083 A1 | 9/2011 | Moll et al. | |
| 2012/0296442 A1 | 11/2012 | Hausman | |
| 2013/0096565 A1 | 4/2013 | Fritzinger | |
| 2013/0172897 A1 | 7/2013 | Dell'Oca et al. | |
| 2013/0245490 A1 | 9/2013 | Strother et al. | |
| 2013/0296733 A1 | 11/2013 | Strother et al. | |
| 2014/0012159 A1 | 1/2014 | Dell'Oca | |
| 2014/0073985 A1 | 3/2014 | Sakai et al. | |
| 2014/0222003 A1 | 8/2014 | Herndon et al. | |
| 2014/0296861 A1 | 10/2014 | McCarthy et al. | |
| 2014/0336473 A1 | 11/2014 | Greco | |
| 2014/0371622 A1 | 12/2014 | Hausman et al. | |
| 2015/0088029 A1 | 3/2015 | Wybo | |
| 2015/0133944 A1 | 5/2015 | Kortenbach | |
| 2016/0374613 A1 | 12/2016 | Kaula et al. | |
| 2018/0195848 A1 | 7/2018 | Rioux et al. | |
| 2018/0252666 A1 | 9/2018 | Fotopoulou et al. | |
| 2018/0256277 A1 | 9/2018 | Garvey et al. | |
| 2018/0360448 A1 | 12/2018 | Harris et al. | |
| 2019/0269420 A1 | 9/2019 | Matusaitis et al. | |
| 2019/0365288 A1 | 12/2019 | Wybo et al. | |
| 2020/0289173 A1 | 9/2020 | Ferree | |
| 2021/0219993 A1 | 7/2021 | Matusaitis et al. | |

FOREIGN PATENT DOCUMENTS

| DE | 202004005657 U1 | 7/2004 |
|---|---|---|
| EP | 1850762 A1 | 11/2007 |

(56) References Cited

FOREIGN PATENT DOCUMENTS

| EP | 3040039 A1 | 7/2016 |
|---|---|---|
| WO | 2005027745 A1 | 3/2005 |

OTHER PUBLICATIONS

Non-Final Office Action issued in U.S. Appl. No. 16/277,247, dated Apr. 29, 2021, 7 pages.
Non-Final Office Action issued in U.S. Appl. No. 16/777,278, dated Apr. 30, 2021, 7 pages.
Australian Examination Report issued in Australian Application 2019231188, dated Dec. 8, 2020, 5 pages.
International Search Report and Written Opinion issued in International Application No. PCT/US2022/015481, dated Apr. 18, 2022, 12 pages.
Checkpoint Surgical, "A Signifcant Advance in Neuroprotective Surgery", Checkpoint Surgical Inc., 2014 (6 Pages).
Checkpoint Surgical, "Nerve Repair: Manual", Checkpoint Surgical Inc., 2016 (44 Pages).
Checkpoint Surgical, "The Next Generation in Neuroprotective Surgical Technology", Checkpoint Surgical Inc., 2014 (6 Pages).
Extended European Search Report issued in European Application No. 17867394.3, dated May 4, 2020 (11 pages).
International Search Report and Written Opinion dated Jun. 13, 2009 for International Application No. PCT/US2019/020709 (10 pages).
International Search Report and Written Opinion dated May 24, 2018 for International Application No. PCT/US2017/059709 (13 Pages).
International Search Report and Written Opinion dated May 24, 2018 for International Application No. PCT/US2017/059714 (13 Pages).
Medartis "Ordering Catalog", Medartis AG, 2017 (100 Pages).
Medartis "Surgical Technique—Step by Step, Aptus Hand", Medartis AG, 2012 (20 Pages).
Medtronic, "Nim-Spine System", Medtronic Sofamor Danek, 2005 (4 Pages).
NuVasive, "An Introduction to NVM5 Nerve Monitoring System" brochure, Jan. 6, 2017 (8 pages).
NuVasive, "XLIF Designed: NVM5" brochure, Jan. 4, 2017 (3 pages).
NuVasive, 510(k) Premarket Notification, NuVasive NVMS System, May 16, 2014 (12 pages).
SpineGuard Press Release, "SpineGuard will launch PediGuard Threaded DSG (TM) device at "SpineWeek 2016 world conference in Singapore, May 9, 2016 (2 pages).
Spineguard, "Clinical Evidence for the Use of PediGuard in Spine Surgery" brochure, May 21, 2012 (5 pages).
Spineguard, "PediGuard" brochure, May 13, 2012 (2 pages).
Surgionix, "Surgical Technique Guide", Surgionix Ltd., 2013 (12 Pages).
Notice of Allowance issued in U.S. Appl. No. 16/292,955, dated Oct. 6, 2020, 8 pages.
Office Action issued in Canadian Application No. 3091925, dated Oct. 8, 2021, 3 pages.
Chinese Office Action issued in Chinese Application No. 201980017384.9, dated Dec. 14, 2021, 8 pages.
English translation of Chinese Office Action issued in Chinese Application No. 201980017384.9, dated Dec. 14, 2022, 9 pages.
Extended European Search Report issued in European Application No. 21171357.3, dated Jul. 23, 2021, 12 pages.
Chinese Office Action issued in Chinese Application No. 201980017384.9, dated May 19, 2021, 11 pages.
English translation of Chinese Office Action issued in Chinese Application No. 201980017384.9, dated May 19, 2021, 12 pages.

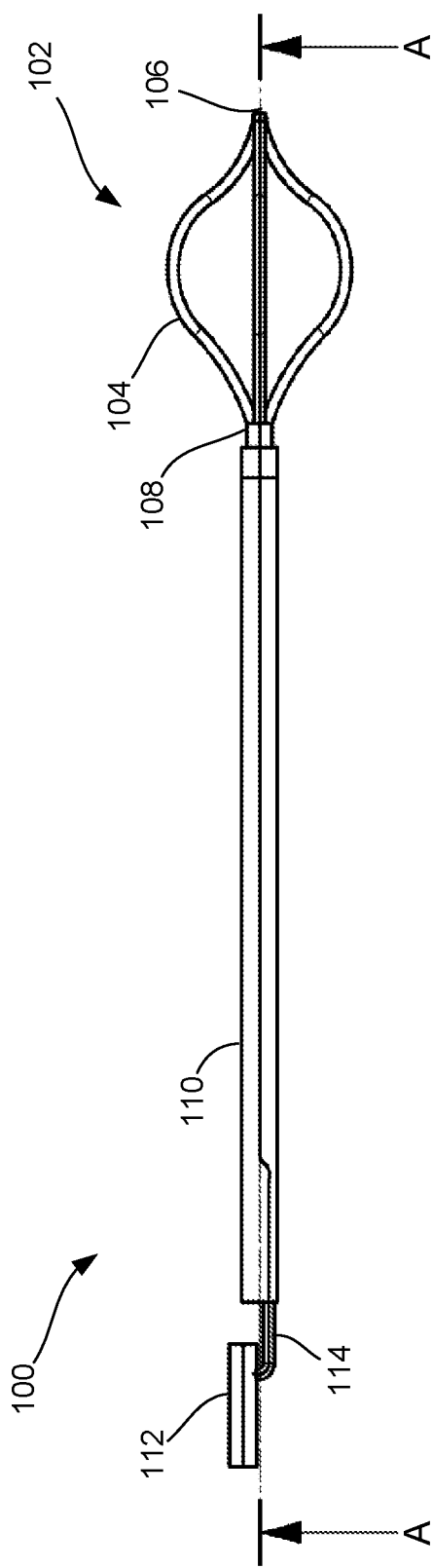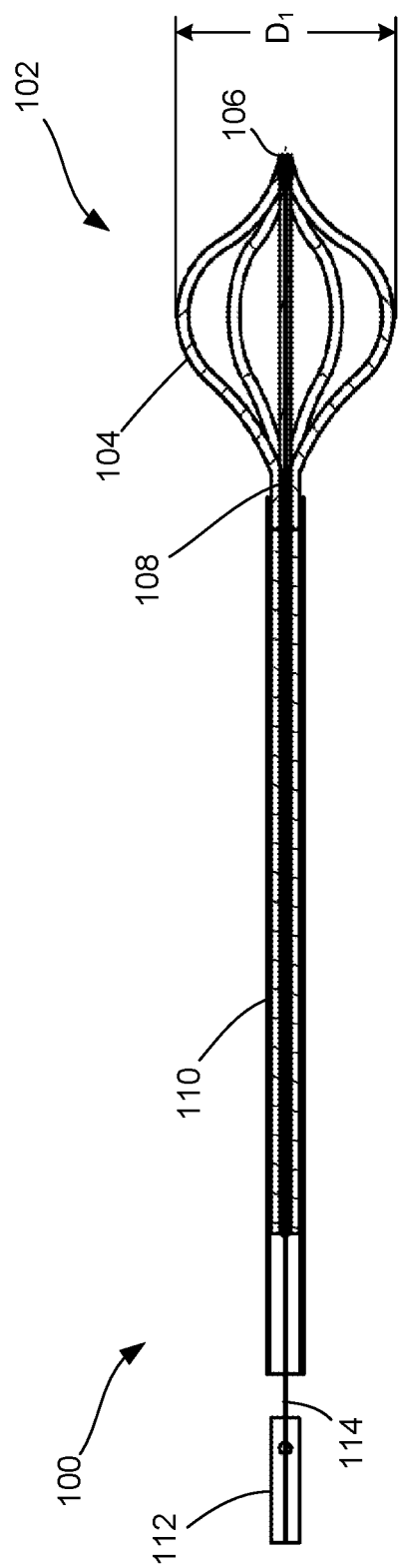
FIG. 2
FIG. 3

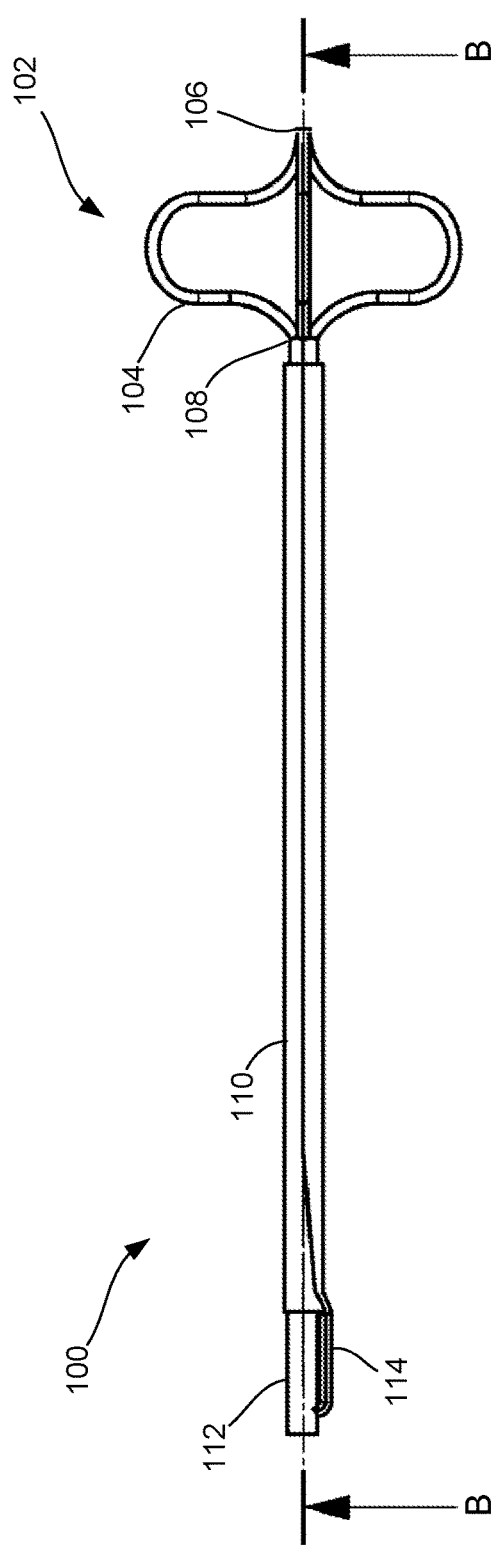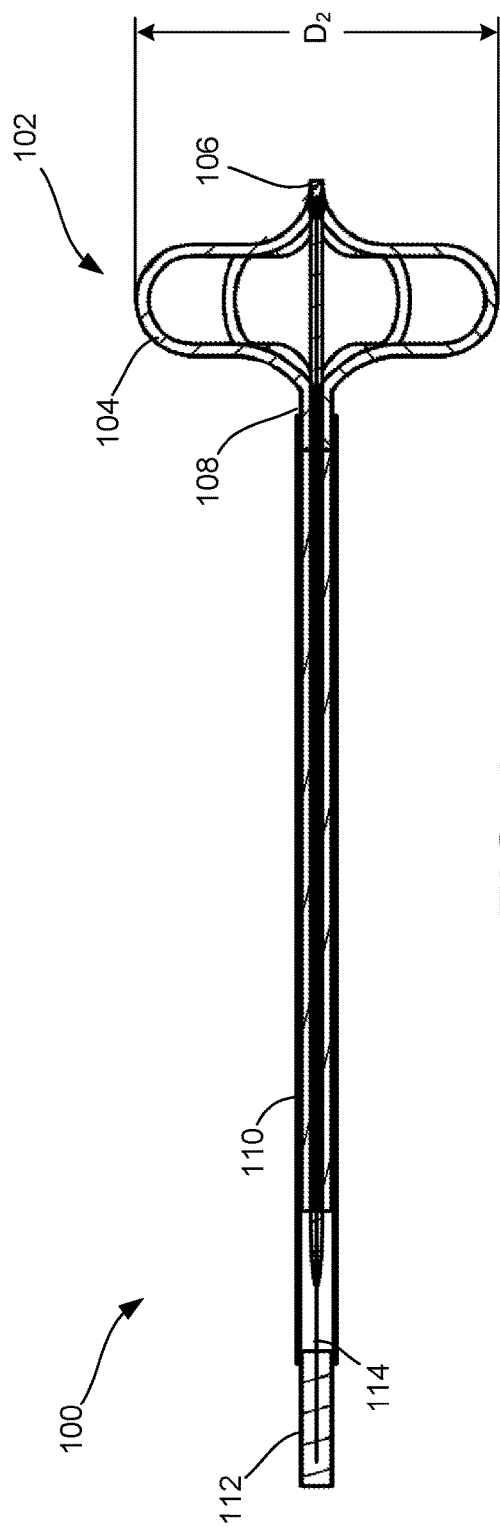

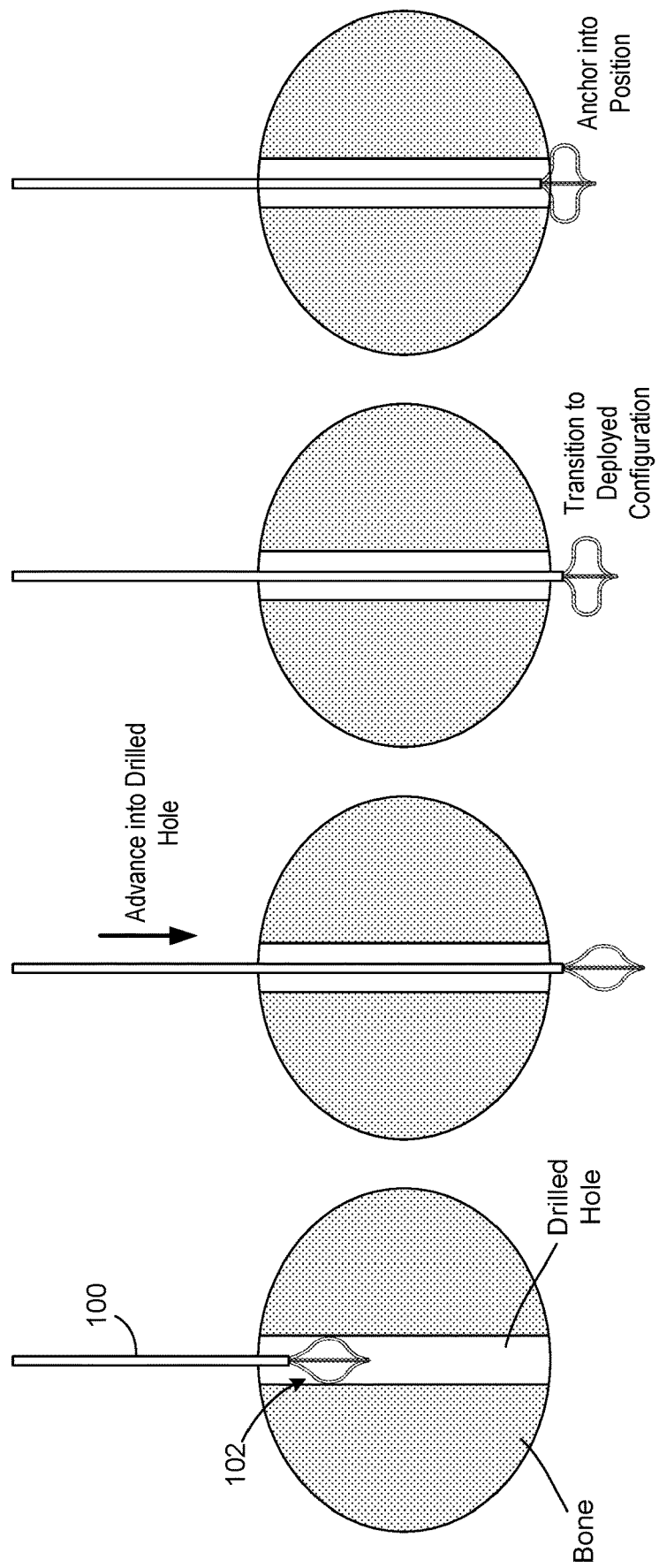

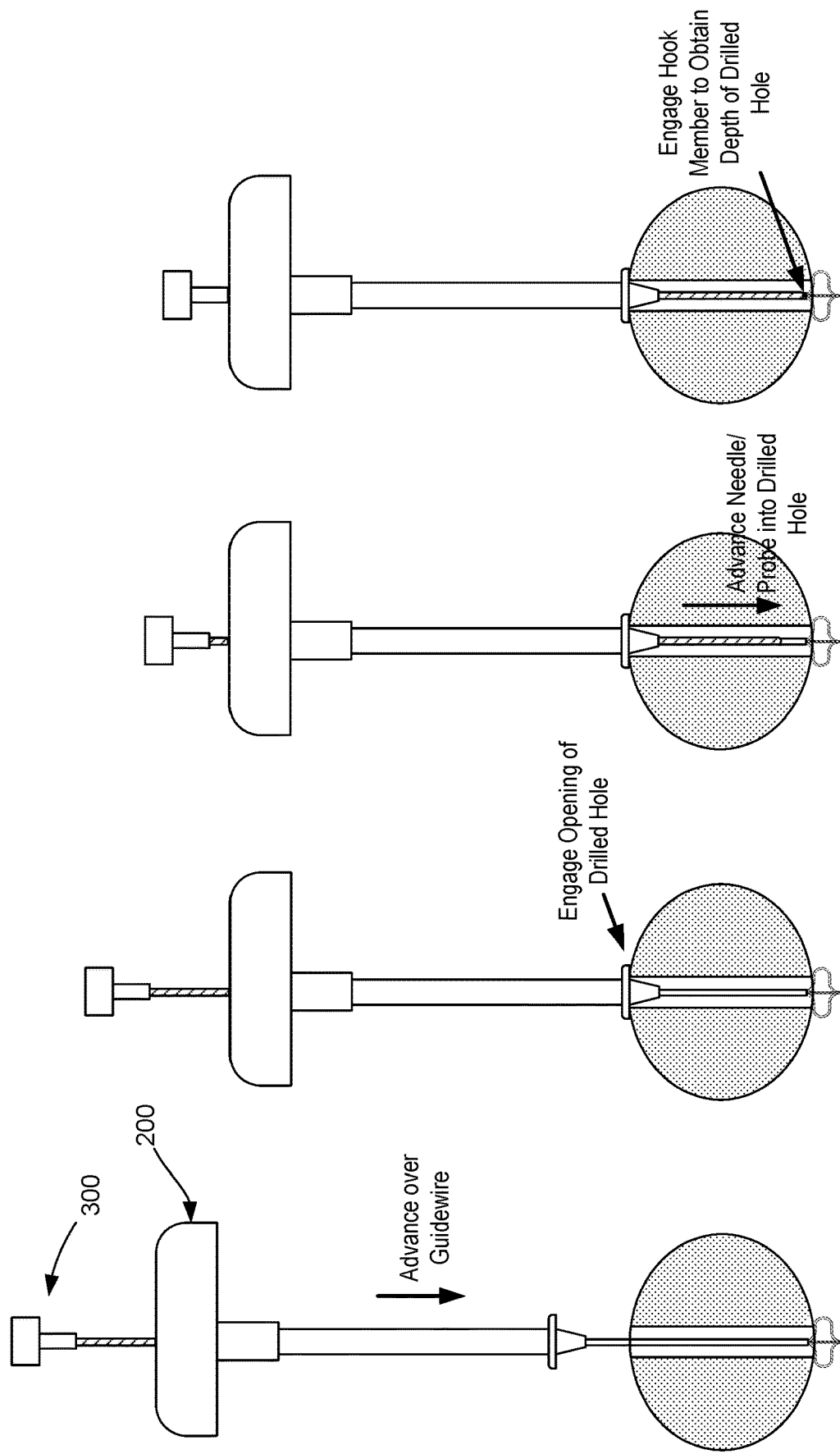

DEVICES FOR MINIMALLY INVASIVE PROCEDURES

CROSS-REFERENCE TO RELATED APPLICATIONS

This application is a divisional of U.S. patent application Ser. No. 16/006,429, filed on Jun. 12, 2018, which claims the benefit of, and priority to, U.S. Provisional Application No. 62/519,845, filed Jun. 14, 2017, the contents of each of which are hereby incorporated by reference herein in their entirety.

FIELD

The present disclosure relates generally to medical devices, and, more particularly, to a measuring system for use in a minimally invasive surgical procedure, such as a bone implant fixation procedure, the measuring system includes a guidewire member having a deployable hook member configured to securely anchor into a desired position relative to a hole drilled in a bone and thereby provide an accurate datum for a measuring instrument for determining a depth of the hole for subsequent screw placement.

BACKGROUND

Orthopedics is a medical specialty concerned with the correction of deformities or functional impairments of the skeletal system, especially the extremities and the spine, and associated structures, such as muscles and ligaments. Some orthopedic surgical procedures require surgeons to secure a device to one or more bones of a patient. For example, in some procedures, the surgeon may span and secures one or more bones, or pieces of a single bone, using a bone plate and one or more fasteners, such as screws. Other bone-related surgical procedures, however, may not require a bone plate and may instead solely rely on the use of one or more screws (e.g., securing a transplanted tendon).

In such bone-related surgical procedures, before an implant or plate, or simply the screw itself, can be attached to bone, an opening is typically drilled into the bone to accommodate the screw. With a hole in place, the surgeon can more easily select a screw of the appropriate length. However, selecting a screw of appropriate length is critical. For example, if the selected screw is too long, the distal end of the screw may pass through the end of the drilled hole and cause damage to the bone and/or protrude entirely through the bone, which can have deleterious effects, such as damage to surrounding tissue and/or pain and discomfort, or more serious complications, for the patient. For example, in some instances, the bone may abut against soft tissues that may be harmed if the screw is too long and may result in irritation of or damage to the soft parts. Additionally, a screw that protrudes through the bone may be tactilely felt by the patient, may prevent soft tissues (e.g., tendons, ligaments, or muscles) from moving over the bone surface as intended, or may even pierce the skin, which can lead to serious infection and complications.

The selection of an appropriate length screw is particularly important in spinal fixation procedures, such as lumbar sacral fusion and the correction of spinal deformities such as scoliotic curves. As an example, a screw mounted in the pedicle portion of the human spine should not extend to a point where the screw contacts the spinal cord itself, an event that can cause irreparable nervous system damage including paralysis. Accordingly, the determination of a length of the hole is important for choosing the appropriate length screw.

During drilling, the surgeon is typically capable of recognizing the resistance on the drill in order to determine when the drill has penetrated through the bone. Because the simple act of drilling does not provide an exact measurement of the depth of the bone itself, a depth gauge is commonly employed for directly measuring the depth of the hole from the top, drilling side to the bottom, opposite side of the hole.

Currently, many designs are known and utilized for measuring the depth of a hole or bore in a portion of a bone. Generally speaking, these designs utilize a central probe member having a barb at a distal end, and a sleeve or channel member. The probe member is inserted into the pilot hole while the surgeon attempts to find the surface with the barb. More specifically, the probe member is inserted to a depth greater than the depth of the pilot hole so that the barb is beyond the opposite side, at which point the surgeon finds the surface by hooking the barb to the opposite side.

The probe member is received in the sleeve or channel member and may reciprocate relative thereto. The channel member has graduated markings along a portion of its length, typically in inches and/or millimeters. A marker is laterally secured to the probe member such that, as the probe member shifts relative to the channel member, the marker indicates the relative shift between the probe member and the channel member. Accordingly, once the probe member has been secured to the opposite side of the bone, the channel member is shifted relative to the probe member and toward the bone until the channel member abuts the surface of the bone. The depth gauge is then read by examining graduated markings indicated by the probe member marker.

A number of problems are experienced with this depth gauge. As an initial point, the components are typically made with surgical-grade stainless steel, and the graduated markings are embossed therein. Therefore, the brightness of the operating room lights on the highly reflective surface can make the markings difficult to read. The markings are commonly in small increments, such as millimeters, and surgeons often have trouble differentiating between the markings, or noting partial increments. Reading these gauges, then, often requires carefully holding the depth gauge as the reading is taken, and a surgeon's effort to closely examine the reading may result in a loss of securement or purchase of the barb on the bone, thus necessitating a re-measurement and a loss of time.

Furthermore, proper reading of the markings requires a surgeon's eyes to be properly aligned with the markings. That is, a proper view of the measurement requires the surgeon to view the gauge from a lateral point of view so that the view of the probe marker aligned with the graduated markings is proper not distorted by the surgeon's elevated, standing perspective. Therefore, it is often necessary for the surgeon to bend over while using these gauges to view an accurate reading. If the depth gauge is tilted in order to make the reading, the sleeve will shift relative to the probe, thus making the measurement inaccurate and possibly causing the barb to become unsecured, as described above. In addition, removal of the depth gauge often causes the measurement to be lost. As the bone is essentially clamped, by light pressure, between the distal end of the channel member and the distal barb of the probe member, it is often necessary to retract the channel member from the bone surface in order to extract the probe from the pilot hole.

SUMMARY

The present disclosure is a medical system for use in a minimally invasive surgical procedure, such as a bone implant fixation procedure, and is configured to provide a faster and more accurate measurement of depth of holes for placement of bone screws and fasteners. The system may be used in any bone implant fixation procedure, including, for example, percutaneous pedicle screw fixation, which may include, but is not limited to, anterior lumbar interbody fusion, lateral interbody fusion, and posterior lumber interbody fusion or transforaminal lumbar interbody fusion.

The medical system includes a guidewire having a deployable distal hook member configured to securely anchor into a desired position relative to a hole drilled in a bone. The distal hook member is configured to transition between a delivery configuration, in which the distal hook member can be positioned within and move through a drilled hole to a desired position, and a deployed configuration, in which the distal hook member is configured to anchor into place, either within the hole (e.g., along a length of a hole, either mono-cortical or bi-cortical, or at the base of a mono-cortical hole) or outside of the hole (e.g., on opposing side of a bi-cortical drilled hole). In particular, the hook member includes a plurality of struts or splines, each of which includes a distal end fixedly coupled to a distal-most end of the guidewire and a proximal end fixedly coupled to a portion of the guidewire body positioned a distance from the distal-most end of the guidewire. Accordingly, the plurality of struts share common fixation points at their respective distal and proximal ends to form a basket-like or mushroom-like structure.

The guidewire further includes a pull-wire or other mechanism coupled to the distal-most end of the guidewire and configured to assist the hook member from transitioning between the delivery and deployed configurations. More specifically, the plurality of struts may be made of a resilient, biologically inert material, such as NITINOL metal, stainless steel, or silicone rubber, for example, and may be arranged either symmetrically or asymmetrically about a longitudinal axis of the hook member. When in the default state (i.e., no application of pulling force upon the pull-wire), the hook member may remain in a delivery configuration, in which the hook member has a relatively compact size and may be freely positioned within a drilled hole or other passage. Due to the resilient nature of the material from which the struts are made from, the hook member may be pushed into a drilled hole until reaching a desired position (i.e., either the bottom of the hole or entirely through the hole if a bicortical drill hole). Upon reaching the desired position, a user (i.e., surgeon or other medical professional) need only apply a pulling force upon the pull-wire, which, in turn, results in retraction of the distal-most end of the guidewire, thereby causing the distal end of each of the plurality of struts coupled thereto to move towards the opposing proximal end of each strut and causing the hook member to expand in diameter and thereby transition to the deployed configuration.

The expansion in diameter of the hook member results in anchoring of the hook member in a desired position. For example, if the hook member is transitioned to the deployed configuration within the drilled hole, the expanded diameter causes the struts to engage interior walls of the drilled hole, thereby lodging the hook member within. In some procedures in which a plate or implant is to be secured with screws through a bicortical drill hole, the distal hook member may be advanced entirely through the hole (from one side of the bone to the other), at which point the surgeon may then transition the hook member to the deployed configuration, in which the expanded diameter is much greater than the drilled hole diameter and opening, and thus the user need only pull back on the guidewire until the expanded hook member securely engages the exterior surface of the bone adjacent to the drilled hole.

The guidewire is configured to assist in depth measurement procedures, as well as the placement of the screw(s) and/or implant(s). For example, the guidewire may be compatible with a variety of separate medical instruments, which may include measuring devices for determining the depth of the hole, as well as other medical instruments used in a bone implant fixation procedure, such as tools for the placement of the screw(s) and/or implant(s). For example, an exemplary measuring instrument may include a sleeve member having a bore extending therethrough and configured to receive the guidewire body. Accordingly, the sleeve member may be slid onto the guidewire, by way of the bore, and may translate along a length of the guidewire, either during positioning and anchoring of the distal hook member or once the distal hook member is deployed and anchored in position. The measuring instrument may further include a needle or probe configured to be slidably mounted within sleeve member, by way of the bore, while the sleeve member is coupled to the guidewire. For example, the bore of the sleeve member may be shaped and/or sized to accommodate both the guidewire body and the needle or probe. Yet still, in other embodiments, the needle or probe may be hollow, such that the needle or probe may receive the guidewire within, thereby allowing for the needle or probe to translate along a length of the guidewire.

Accordingly, once the hook member is anchored in place, the guidewire provides improved stability during a depth measurement procedure and/or screw placement procedure, as the guidewire essentially acts as a guide for the sleeve member and/or needle or probe to slide along a length thereof. Furthermore, the hook member provides an accurate datum from which the depth of the hole can be determined, thereby improving the precision with which depths of holes can be determined. For example, upon establishing an anchored position with the hook member, a user need only slide the sleeve member towards the drilled hole until a distal-most end of the slide member, which is tapered, engages the opening of the hole and establishes engagement and maintains the sleeve member in a stabilized position, at which point, the needle or probe can be used for measuring the depth of the hole.

The measuring instrument further includes at least one sensor configured to generate an electronic signal indicative of a depth of the hole as a result of sensing a distance of movement of the needle or probe into the drilled hole. For example, in one embodiment, a surgeon need only advance the needle or probe into the hole until they establish engagement between the distal tip of the needle or probe with the anchored hook member. Again, the guidewire essentially acts as a guide upon which the needle or probe may either slide over, or slide alongside, when advancing to the anchored hook member, which provides the datum from which the depth of the hole is determined.

The sensor is configured to generate an electronic signal based on a distance of movement of needle or probe member, wherein the electronic signal is indicative of at least a depth of the hole. In particular, the sensor may include inductive or capacitive elements or assemblies configured to sense the location of the distal tip of the needle or probe relative to a distal end of the sleeve member, and, as a result, generate an electronic signal representing the distance therebetween. Accordingly, the sensed distance between the distal end of the sleeve member (when abutting the bone surface) and the distal tip of the needle or probe member (when abutting the anchored hook member) is the depth of the hole. In some embodiments, the sensor system may include a potentiometer arrangement. In some embodiments, the sensor system for determining depth may include a worm gear measurement system, wherein the sleeve member may include a pinion gear and the needle or probe may have a corresponding worm gear configuration. Yet still, in some embodiments, the sensor system may include a laser diode configured to read or otherwise sense machine-readable markings on the needle or probe to determine distance traveled when determining/calculating depth of the drilled hole.

It should be noted that the device may include logic or allow for adjustment to the sensing capabilities so as to program the sensor to account for other variables when sensing the depth of the hole. For example, in some embodiments, certain procedures require fixing a plate or implant to the bone via screws. Accordingly, the screw length must not only be sufficient to fill the hole but also long enough to account for the thickness of a plate or implant through which it passes when engaging the hole. Accordingly, in some embodiments, the sensor may be programmed so as to account for the thickness of the plate or implant and will further include that thickness in the electronic signal produced, such that the electronic signal is indicative of the total depth that a corresponding screw length will need to cover, including the depth of the hole in the bone in addition to the thickness of the plate or implant through which the screw will pass through and the screw head will engage.

Accordingly, the digital sensing of the hole depth provides a much more accurate measurement than conventional analog depth gauges and also requiring very little, if any, input or interpretation from the surgeon. Accordingly, by providing a much more accurate measurement of a hole depth, the surgeon is able to select the correct length screw for any given hole so as to improve the chances of a successful surgery.

In some embodiments, the measuring instrument may further include a display provided on the body and configured to visually provide a digital readout of a depth measurement of the hole based on the electronic signal from the sensor. In other embodiments, the measuring instrument may be configured to wirelessly communicate and exchange data with a separate display or computing device, such as, for example, a monitor or panel display, a PC, a notebook, a tablet computer, a smartphone, or other wireless computing device.

Upon receiving the electronic signal from the sensor, the separate display or computing device may be configured to visually provide the depth measurement of the hole based on the electronic signal from the sensor. Furthermore, in some embodiments, the computing device may include a specific software application that may be directed to maintaining a record of the hole measurements and/or provide an interactive user interface in which multiple holes can be mapped to a particular plate or implant and the depth of each hole (including the thickness of the plate or implant) can be included and stored for records.

BRIEF DESCRIPTION OF THE DRAWINGS

Features and advantages of the claimed subject matter will be apparent from the following detailed description of embodiments consistent therewith, which description should be considered with reference to the accompanying drawings, wherein:

FIG. 2 is a side view of the guidewire assembly of FIG. 1;

FIG. 3 is a side cross-sectional view of the guidewire assembly taken along lines A-A of FIG. 2;

FIG. 5 is a side view of the guidewire assembly of FIG. 4;

FIG. 6 is a side cross-sectional view of the guidewire assembly taken along lines B-B of FIG. 5;

FIGS. 14A-14H illustrate a series of steps for performing a procedure of deploying the hook member of the guidewire and subsequently obtaining a depth measurement using the surgical depth instrument consistent with the present disclosure.

Figure 1:
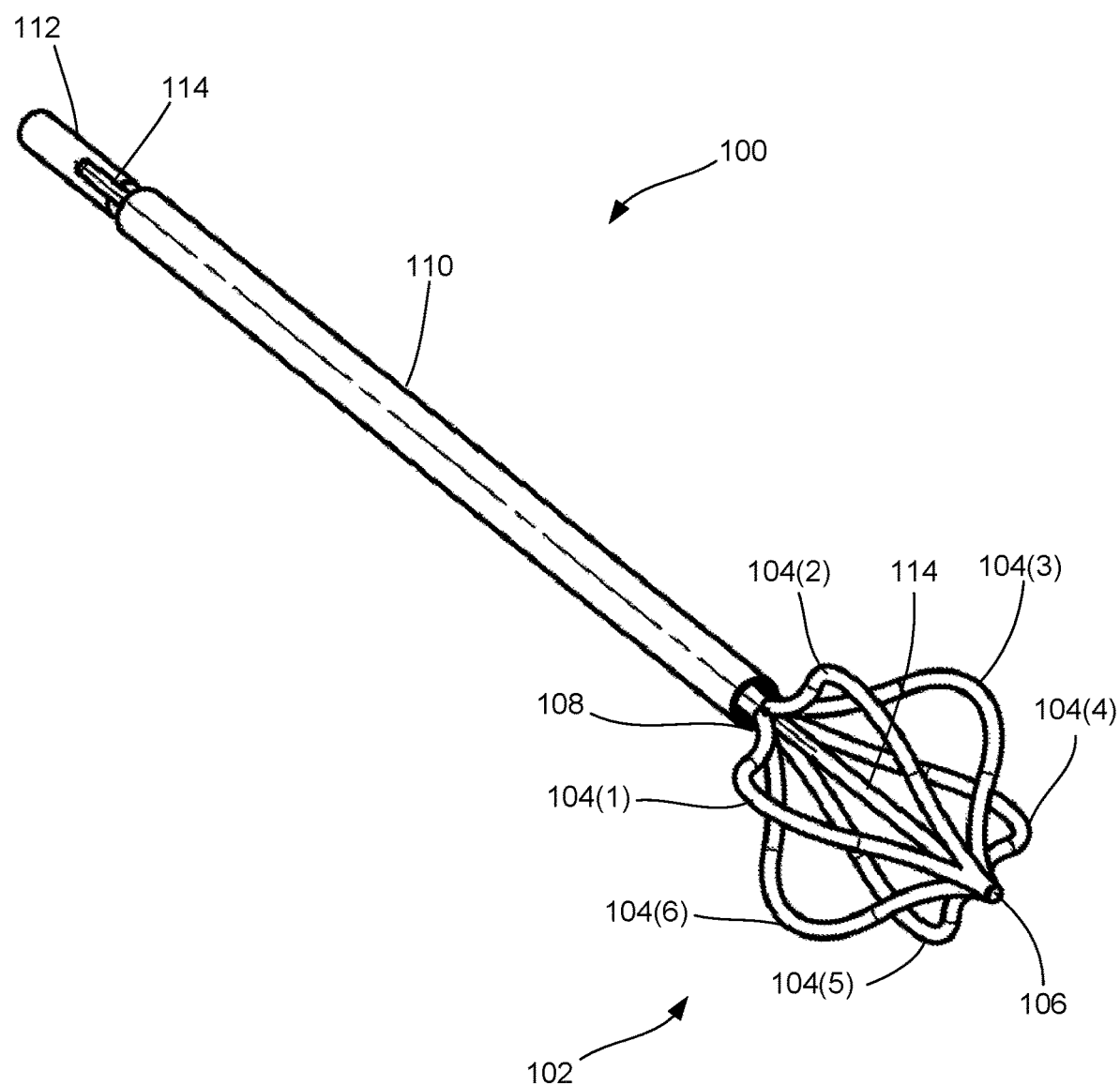
FIG. 1 is perspective view of one embodiment of a guidewire assembly of the minimally invasive surgical depth instrument consistent with the present disclosure, illustrating the distal hook member in the delivery configuration.

For a thorough understanding of the present disclosure, reference should be made to the following detailed description, including the appended claims, in connection with the above-described drawings. Although the present disclosure is described in connection with exemplary embodiments, the disclosure is not intended to be limited to the specific forms set forth herein. It is understood that various omissions and substitutions of equivalents are contemplated as circumstances may suggest or render expedient.

DETAILED DESCRIPTION

By way of overview, the present disclosure is generally directed to a medical system for use in a minimally invasive surgical procedure, such as a bone implant fixation procedure, and is configured to provide a faster and more accurate measurement of depth of holes for placement of bone screws and fasteners. The system may be used in any bone implant fixation procedure, including, for example, percutaneous pedicle screw fixation, which may include, but is not limited to, anterior lumbar interbody fusion, lateral interbody fusion, and posterior lumber interbody fusion or transforaminal lumbar interbody fusion.

The medical system includes a guidewire having a deployable distal hook member configured to securely anchor into a desired position relative to a hole drilled in a bone. The distal hook member is configured to transition between a delivery configuration, in which the distal hook member can be positioned within and move through a drilled hole to a desired position, and a deployed configuration, in which the distal hook member is configured to anchor into place, either within the hole (e.g., at the base of a monocortical hole) or outside of the hole (e.g., on opposing side of a bi-cortical drilled hole). In particular, the hook member includes a plurality of struts or splines, each of which includes a distal end fixedly coupled to a distal-most end of the guidewire and a proximal end fixedly coupled to a portion of the guidewire body positioned a distance from the distal-most end of the guidewire. Accordingly, the plurality of struts share common fixation points at their respective distal and proximal ends to form a basket-like or mushroom-like structure.

The guidewire further includes a pull-wire or other mechanism coupled to the distal-most end of the guidewire and configured to assist the hook member from transitioning between the delivery and deployed configurations. More specifically, the plurality of struts may be made of a resilient, biologically inert material, such as NITINOL metal, stainless steel, or silicone rubber, for example, and may be arranged either symmetrically or asymmetrically about a longitudinal axis of the hook member. When in the default state (i.e., no application of pulling force upon the pull-wire), the hook member may remain in a delivery configuration, in which the hook member has a relatively compact size and may be freely positioned within a drilled hole or other passage. Due to the resilient nature of the material from which the struts are made from, the hook member may be pushed into a drilled hole until reaching a desired position (i.e., either the bottom of the hole or entirely through the hole if a bicortical drill hole). Upon reaching the desired position, a user (i.e., surgeon or other medical professional) need only apply a pulling force upon the pull-wire, which, in turn, results in retraction of the distal-most end of the guidewire, thereby causing the distal end of each of the plurality of struts coupled thereto to move towards the opposing proximal end of each strut and causing the hook member to expand in diameter and thereby transition to the deployed configuration.

The expansion in diameter of the hook member results in anchoring of the hook member in a desired position relative to the drilled hole. For example, if the hook member is transitioned to the deployed configuration within the drilled hole, the expanded diameter causes the struts to engage interior walls of the drilled hole, thereby lodging the hook member within the hole at a desired position within the hole. This may be advantageous when cannulated screws are to be used, such that a cannulated screw can essentially ride along the guidewire when placed within the hole. In some procedures in which a plate or implant is to be secured with screws through a bicortical drill hole, the distal hook member may be advanced entirely through the hole (from one side of the bone to the other), at which point the surgeon may then transition the hook member to the deployed configuration, in which the expanded diameter is much greater than the drilled hole diameter and opening, and thus the user need only pull back on the guidewire until the expanded hook member securely engages the exterior surface of the bone adjacent to the drilled hole.

The guidewire is configured to assist in depth measurement procedures, and may further be configured to assist in the placement of the screw(s) and/or implant(s). For example, the guidewire may be compatible with a variety of separate medical instruments, which may include measuring devices for determining the depth of the hole, as well as other medical instruments used in a bone implant fixation procedure, such as tools for the placement of the screw(s) and/or implant(s). For example, an exemplary surgical depth instrument may include a sleeve member having a bore extending therethrough and configured to receive the guidewire body.

Accordingly, the sleeve member may be slid onto the guidewire, by way of the bore, and may translate along a length of the guidewire, either during positioning and anchoring of the distal hook member or once the distal hook member is deployed and anchored in position. The measuring instrument may further include a needle or probe configured to be slidably mounted within sleeve member, by way of the bore, while the sleeve member is coupled to the guidewire. For example, the bore of the sleeve member may be shaped and/or sized to accommodate both the guidewire body and the needle or probe. Yet still, in other embodiments, the needle or probe may be hollow, such that the needle or probe may receive the guidewire within, thereby allowing for the needle or probe to translate along a length of the guidewire.

Accordingly, once the hook member is anchored in place, the guidewire provides improved stability during a depth measurement procedure and/or screw placement procedure, as the guidewire essentially acts as a guide for the sleeve member and/or needle or probe to slide along a length thereof. Furthermore, the hook member provides an accurate datum from which the depth of the hole can be determined, thereby improving the precision with which depths of holes can be determined. For example, upon establishing an anchored position with the hook member, a user need only slide the sleeve member towards the drilled hole until a distal-most end of the slide member, which is tapered, engages the opening of the hole and establishes engagement and maintains the sleeve member in a stabilized position, at which point, the needle or probe can be used for measuring the depth of the hole.

FIG. 1 is perspective view of one embodiment of a guidewire assembly 100 consistent with the present disclosure. FIG. 2 is a side view of the guidewire assembly 100 and FIG. 3 is a side cross-sectional view of the guidewire assembly 100 taken along lines A-A of FIG. 2. The guidewire assembly 100 generally includes a deployable hook member 102 at a distal end of the guidewire 100. The distal hook member 102 includes a plurality of struts or splines 104(1)-104(6), each of which includes a distal end fixedly coupled to a distal-most end 106 of the guidewire 100 and a proximal end fixedly coupled to a portion of the guidewire body 108 positioned a distance from the distal-most end 106. Accordingly, the plurality of struts 106 share common fixation points at their respective distal and proximal ends to form a basket-like or mushroom-like structure.

The plurality of struts 104 may be made of a resilient, biologically inert material, such as NITINOL metal, stainless steel, or silicone rubber, for example, and may be arranged either symmetrically or asymmetrically about a longitudinal axis of the hook member 102. Although shown with a total of six struts 104(1), 104(2), 104(3), 104(4), 104(5), and 104(6), it should be noted that a hook member 102 consistent with the present disclosure may include more or less than six struts and is thus not limited to any number of struts.

Figure 4:
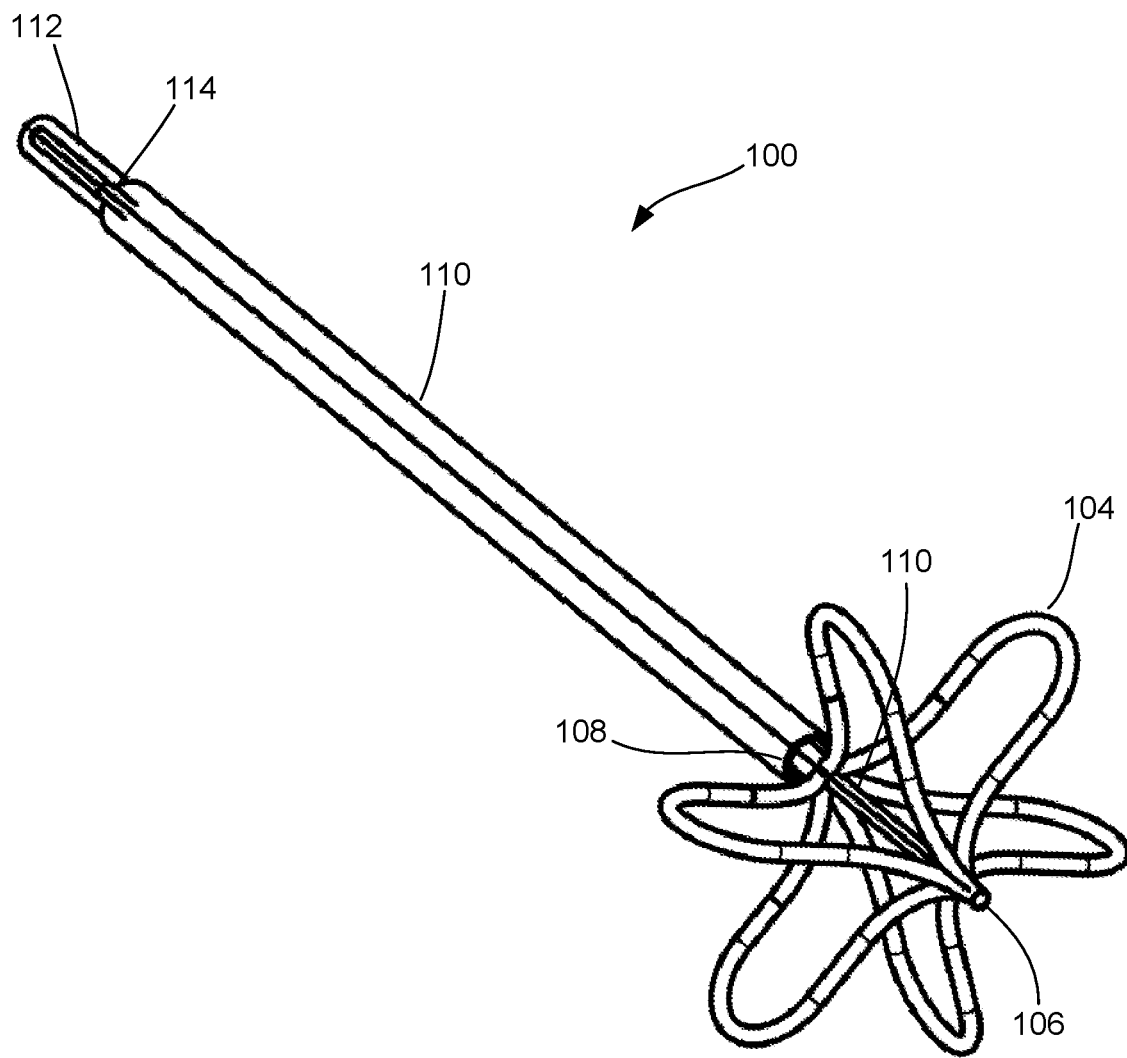
FIG. 4 is perspective view of the guidewire assembly illustrating the distal hook member in the deployed configuration.

The hook member 102 is configured to transition between a delivery configuration, as illustrated in FIGS. 1-3, and a deployed configuration, as shown in FIGS. 4-6. In particular, guidewire assembly 100 may further include a guide tube or cover 110 configured to provide rigidity to the guidewire 100 during positioning in a drilled hole, a pull rod 112, and a pull-wire 114 coupled to the pull rod 112 and coupled to the distal-most end 106 of the guidewire 100. The pull rod 112 and pull-wire 114 are configured to assist the hook member 102 from transitioning between the delivery and deployed configurations. For example, when in the default state (i.e., no application of pulling force upon the pull-rod 112 and pull-wire 114), the hook member 102 may remain in a delivery configuration, in which the hook member 102 has a relatively compact size and has a first diameter $D_1$. When in the delivery configuration and due to its compact size, the hook member 102 may be freely positioned within and move through a drilled hole or other passage to a desired position. Due to the resilient nature of the material from which the struts are made from, the hook member 102 may be pushed into a drilled hole until reaching a desired position (i.e., either the bottom of the hole or entirely through the hole if a bicortical drill hole).

Upon reaching the desired position, a user (i.e., surgeon or other medical professional) need only apply a pulling force upon the pull-wire 114 (i.e., pull the pull rod 112), which, in turn, results in retraction of the distal-most end 106 of the guidewire 100, thereby causing the distal end of each of the plurality of struts 104 coupled thereto to move towards the opposing proximal end of each strut and cause the hook member 102 to expand in diameter and thereby transition to the deployed configuration, as shown in FIGS. 4-6. For example, when in the deployed configuration, the hook member 102 has a second diameter $D_2$ which is greater than the first diameter $D_1$ when the hook member 102 is in the delivery configuration.

Figure 7B:
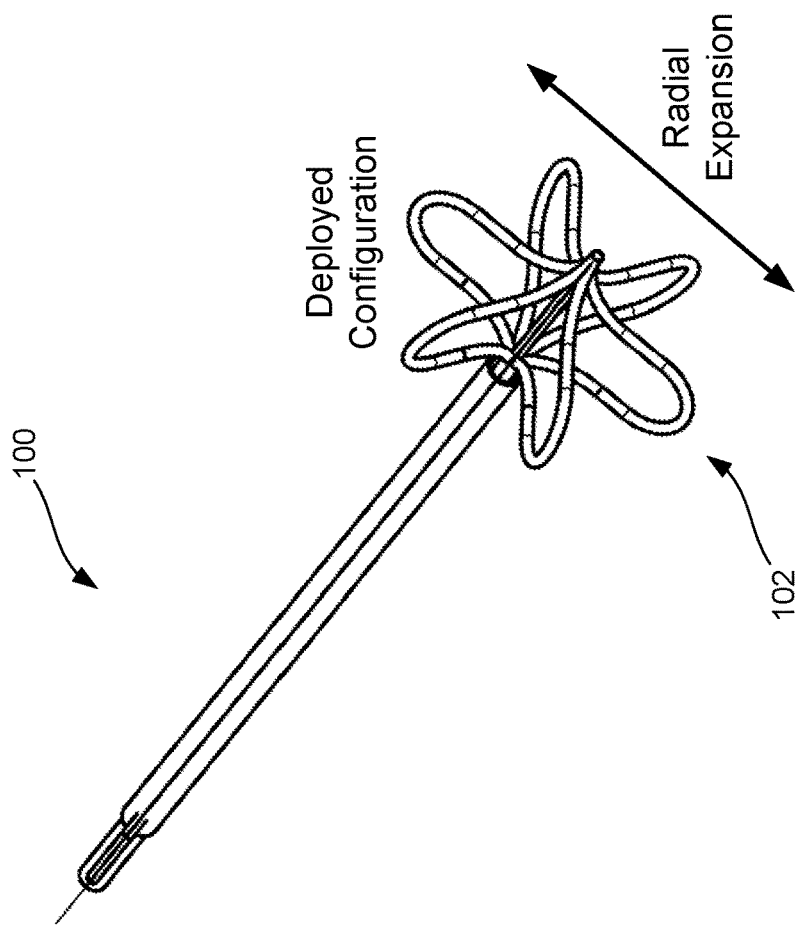
FIGS. 7A and 7B are perspective views of the guidewire assembly illustrating the transition of the distal hook member from the delivery configuration (FIG. 7A) to the deployed configuration (FIG. 7B)
Figure 7A:
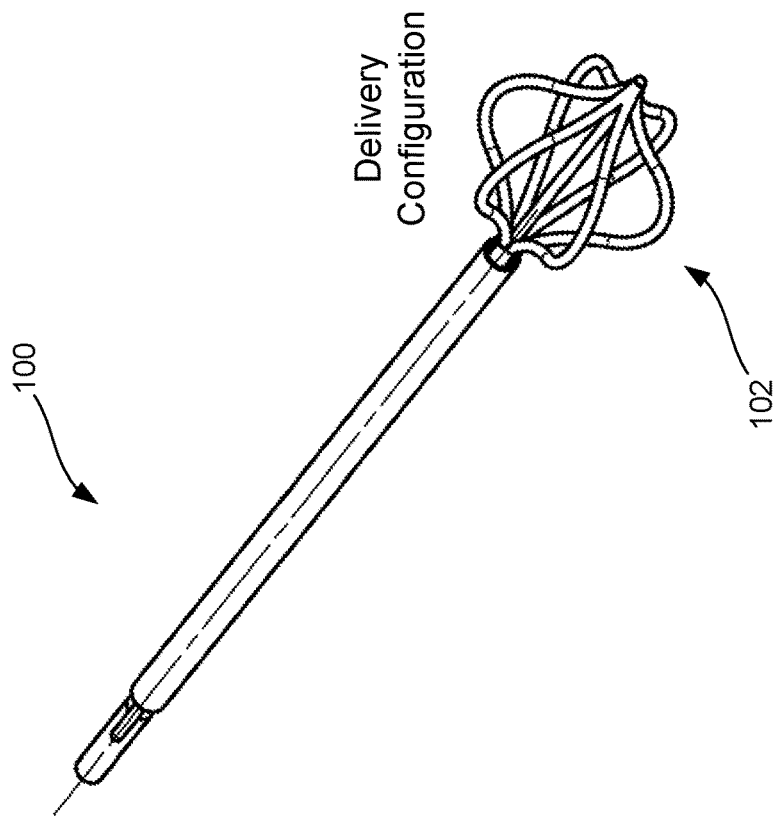

FIGS. 7A and 7B are perspective views of the guidewire 100 illustrating the transition of the hook member 102 from the delivery configuration (FIG. 7A) to the deployed configuration (FIG. 7B). The expansion in diameter of the hook member 102 results in anchoring of the hook member 102 in a desired position. When in the deployed configuration, the hook member 102 is configured to anchor into place, either within the hole (e.g., at the base of a mono-cortical hole) or outside of the hole (e.g., on opposing side of a bi-cortical drilled hole). For example, if the hook member 102 is transitioned to the deployed configuration within the drilled hole, the expanded diameter causes the struts 104 to engage interior walls of the drilled hole, thereby lodging the hook member 102 within. In some procedures in which a plate or implant is to be secured with screws through a bicortical drill hole, the distal hook member may be advanced entirely through the hole (from one side of the bone to the other), at which point the surgeon may then transition the hook member to the deployed configuration, in which the expanded diameter is much greater than the drilled hole diameter and opening, and thus the user need only pull back on the guidewire 100 until the expanded hook member 102 securely engages the exterior surface of the bone adjacent to the drilled hole. Due to the resilient nature of the material of the struts, the hook member may essentially flatten against the surface of the bone upon a user pulling back on the guidewire, wherein such flattening may enhance tactile feel, providing the user with an indication that the hook member is sufficiently anchored. The user can maintain the tension on the pull-wire 114 by simply winding a portion of the pull-wire 114 around the pull rod 112 and subsequently reestablishing a connection between the pull rod 112 and the need only position the pull rod 112 in the guide tube or cover 114, as shown in FIGS. 5 and 6. When the user wishes to disengage the hook member 102 from an anchored position, they need only release the tension on the pull-wire 114 and the struts 104 will return to their default shape, thereby returning the hook member 102 to the delivery configuration, at which point the guidewire 100 can be removed.

The guidewire 100 is configured to assist in depth measurement procedures, as well as the placement of the screw(s) and/or implant(s). For example, the guidewire may be compatible with a variety of separate medical instruments, which may include measuring devices for determining the depth of the hole, as well as other medical instruments used in a bone implant fixation procedure, such as tools for the placement of the screw(s) and/or implant(s).

Figure 8:
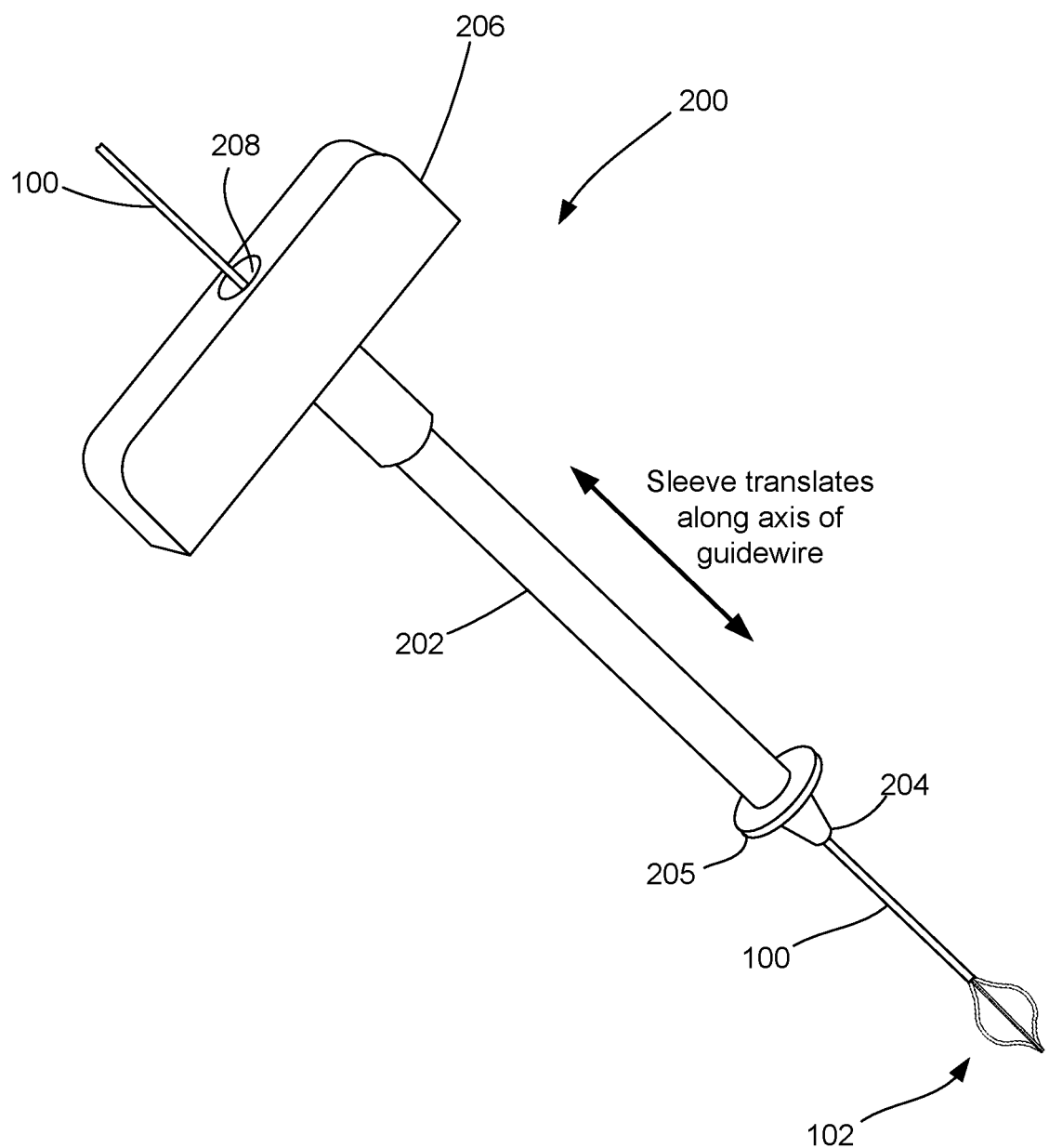
FIG. 8 is a perspective view of a sleeve member of the surgical depth instrument consistent with the present disclosure, illustrating the sleeve member slidably mounted to the guidewire assembly.
Figure 9:
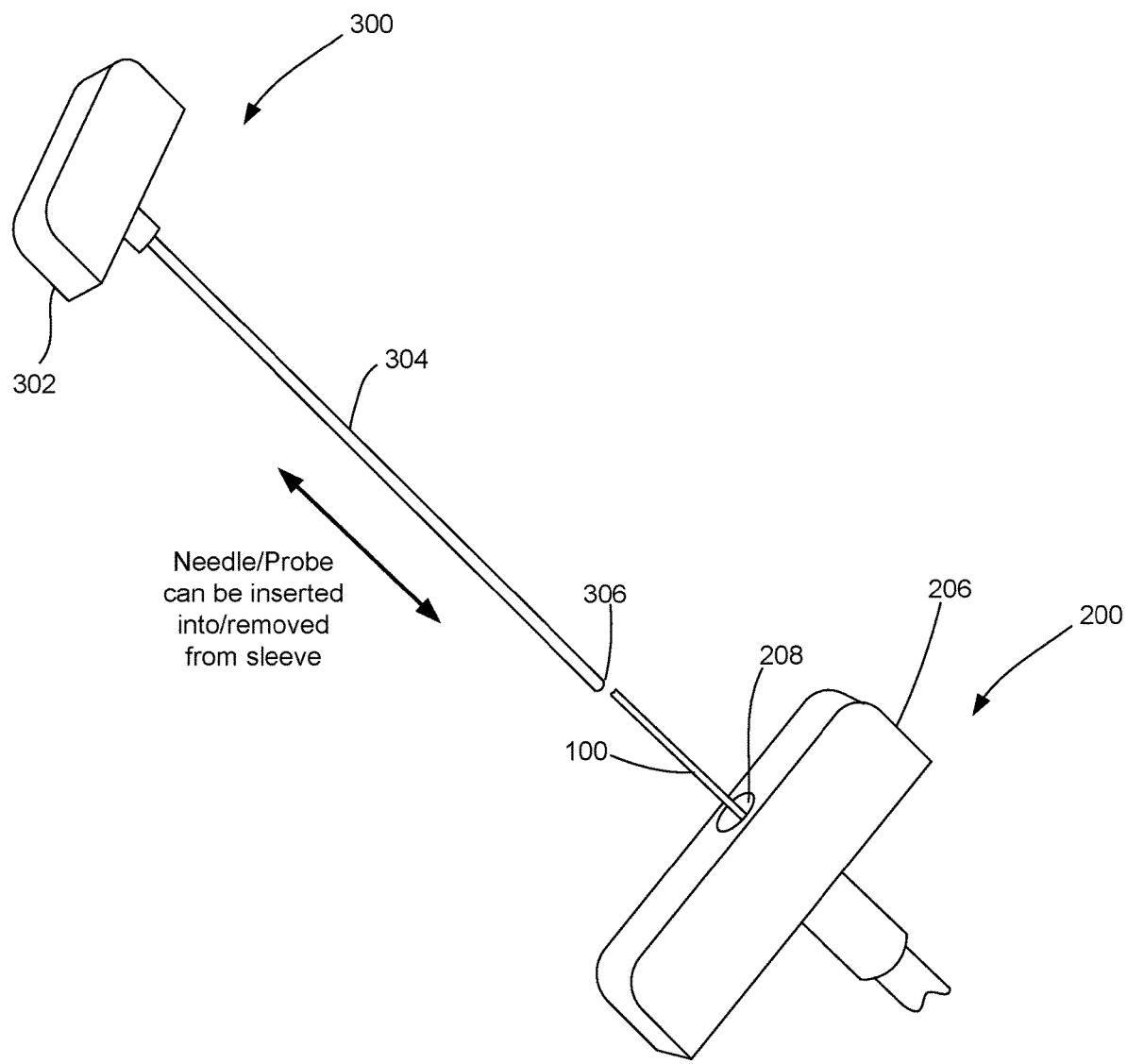
FIG. 9 is a perspective view of the needle or probe member of the surgical depth instrument relative to the corresponding sleeve member.

For example, an exemplary measuring or surgical depth instrument may include a sleeve member 200 and a needle or probe member 300 compatible for use with the guidewire 100. FIG. 8 is a perspective view of the sleeve member 200 slidably mounted to the guidewire 100 and FIG. 9 is a perspective view of the needle or probe member 300 of the surgical depth instrument relative to the corresponding sleeve member 200.

As shown, the sleeve member 200 generally includes an elongate body 202, which may serve as a handle for the user during a procedure, wherein the body 202 has a distal end 204 and a proximal end 206, as well as a bore 208 extending entirely through the body 202 from the distal end 204 to the proximal end 206. The bore 208 is shaped and/or sized to receive the guidewire body therein. Accordingly, the sleeve member 200 may be slid onto the guidewire 100, by way of the bore 208, and may thereby translate along a length of the guidewire 100, either during positioning and anchoring of the distal hook member 102 or once the distal hook member 102 is deployed and anchored in position. As will be described in greater detail herein, the distal end 204 of the sleeve member 200 is configured to engage at least an opening of a drilled hole during a procedure and a flanged member 205 generally serves as a abutting feature for engaging the exterior surface of the bone along a periphery of the hole opening.

The surgical depth instrument may further include a needle or probe 300. The needle or probe 300 includes a handle 302, an elongate body 304 extending from the handle 302, and a distal tip 306. For sake of clarity and ease of description, the needle or probe 300 is hereinafter referred to as "probe 300". The probe 300 is configured to be slidably mounted within the sleeve member 200, by way of the bore 208, while the sleeve member 200 is coupled to the guidewire 100. For example, the bore 208 of the sleeve member 200 may be shaped and/or sized to accommodate both the guidewire 100 and the probe 300. Yet still, in other embodiments, the probe 300 may be hollow, such that the probe 300 may receive the guidewire 100 within, thereby allowing for the probe 300 to translate along a length of the guidewire 100 and further slide along a length of the sleeve member 200.

Accordingly, once the hook member 102 is anchored in place, the guidewire 100 provides improved stability during a depth measurement procedure and/or screw placement procedure, as the guidewire 100 essentially acts as a guide for the sleeve member 200 and/or probe 300 to slide along a length thereof. Furthermore, the hook member 100 provides an accurate datum from which the depth of the hole can be determined, thereby improving the precision with which depths of holes can be determined.

For example, upon establishing an anchored position with the hook member 102, a user need only slide the sleeve member 200 towards the drilled hole until a distal-most end 204 of the slide member 200, which is tapered, engages the opening of the hole and establishes engagement and maintains the sleeve member 200 in a stabilized position, at which point, the probe 300 can be used for measuring the depth of the hole. In some embodiments, the distal end 204 may further include edges or prongs that, upon rotation of the sleeve member 200, can stick into the interior surface of the hole and thereby further establish purchase with the bone and prevent inadvertent dislodging from the hole. In order to remove the sleeve member, the user need only rotate the sleeve member in the opposite direction, which will release the edges or prongs from engagement.

Figure 10A:
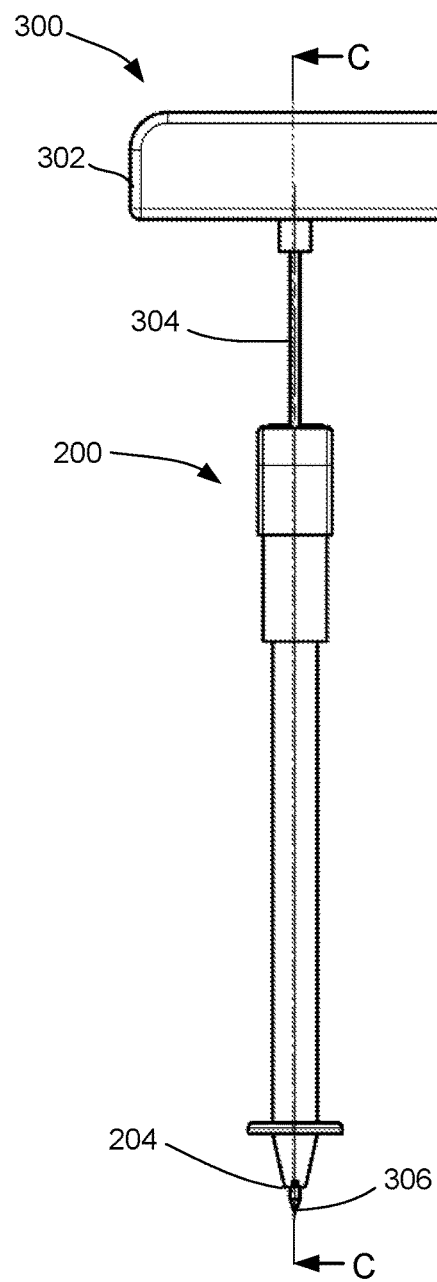
FIGS. 10A and 10B are side views of an assembled surgical depth instrument consistent with the present disclosure illustrating movement of the needle or probe from a starting position (FIG. 10A) to an extended position (FIG. 10B) for measurement of a hole depth.
Figure 10B:
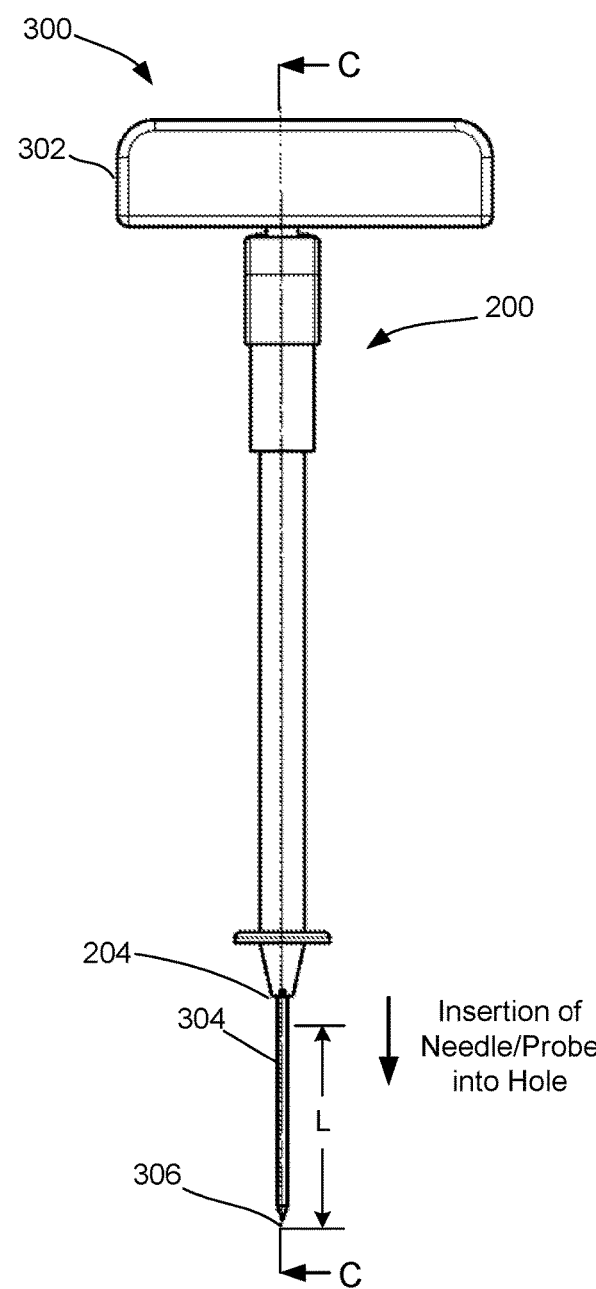
Figure 11A:
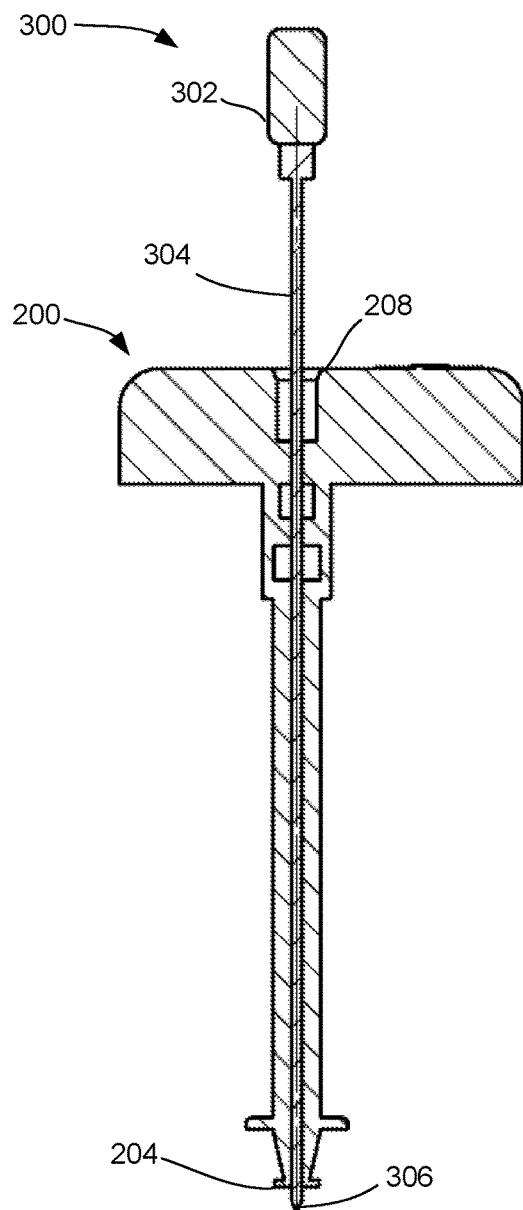
FIGS. 11A and 11B are side cross-sectional views of the assembled surgical depth instrument taken along lines C-C of FIGS. 10A and 10B, respectively.
Figure 11B:
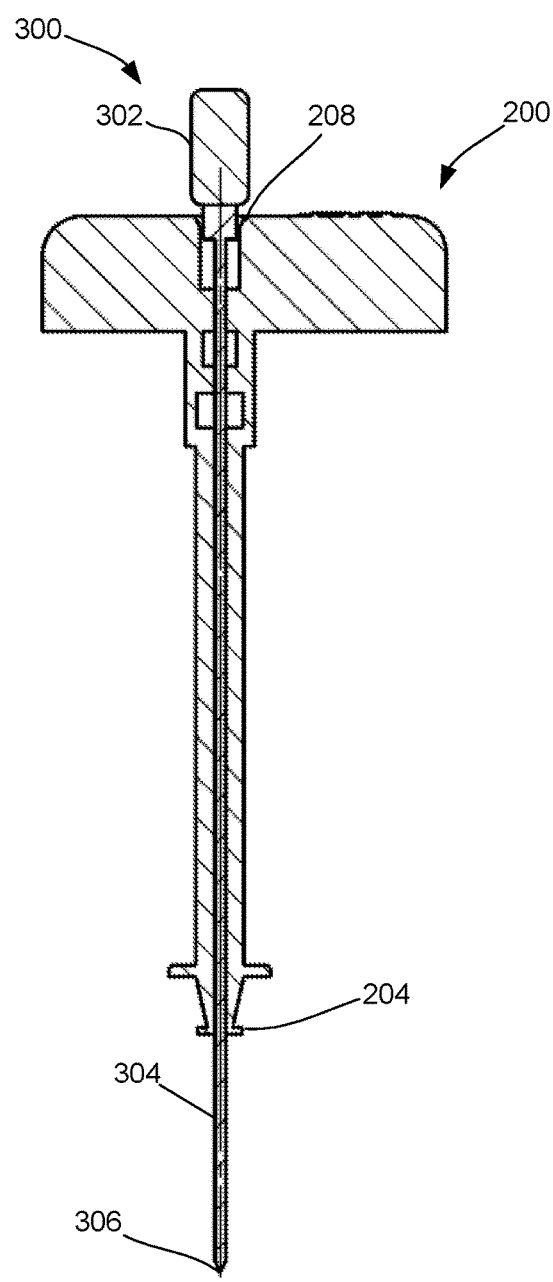

FIGS. 10A and 10B are side views of the sleeve member 200 and probe 300 assembled with one another illustrating movement of the needle or probe from a starting position (FIG. 10A) to an extended position (FIG. 10B) for measurement of a hole depth. FIGS. 11A and 11B are side cross-sectional views of the sleeve member 200 and probe 300 assembled with one another taken along lines C-C of FIGS. 10A and 10B, respectively. The surgical depth instrument further includes at least one sensor configured to generate an electronic signal indicative of a depth of the hole as a result of sensing a distance of movement of the probe 300 into the drilled hole. For example, as will be described in greater detail herein, a surgeon need only advance the probe 300 into the hole until they establish engagement between the distal tip 306 of the probe 300 with the anchored hook member 102. Again, the guidewire 100 essentially acts as a guide upon which the probe 300 may either slide over, or slide alongside, when advancing to the anchored hook member 102, which provides the datum from which the depth of the hole is determined.

The sensor is configured to generate an electronic signal based on a distance of movement of the probe 300, wherein the electronic signal is indicative of at least a depth of the hole. In particular, the sensor may include inductive or capacitive elements or assemblies configured to sense the location of the distal tip 306 of the probe 300 relative to a distal end 204 of the sleeve member 200, and, as a result, generate an electronic signal representing the distance therebetween. Accordingly, the sensed distance between the distal end 204 of the sleeve member 200 (when abutting the bone surface) and the distal tip of the probe member (when abutting the anchored hook member) is the depth of the hole.

Figure 12:
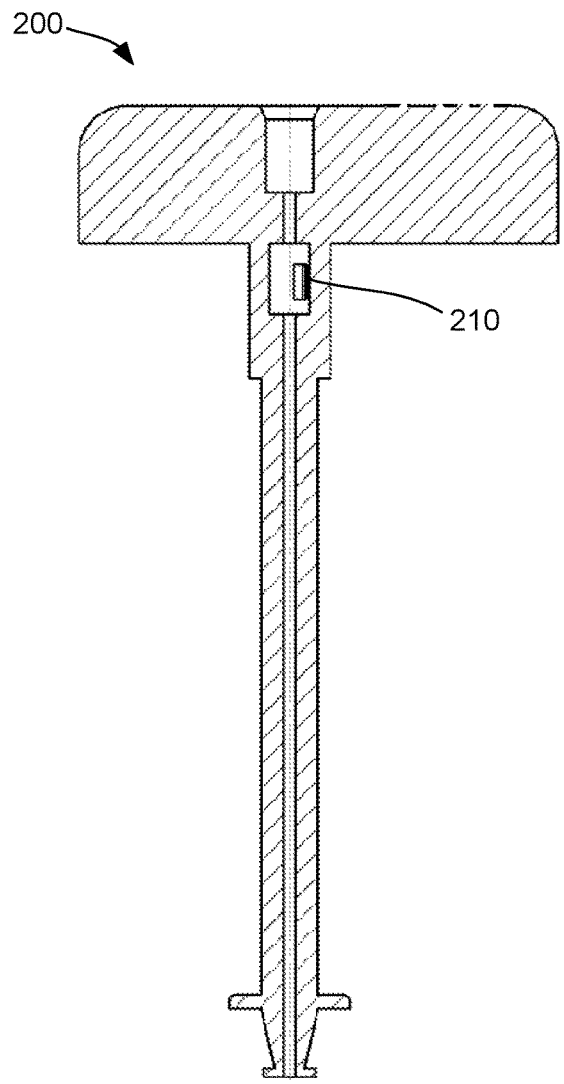
FIGS. 12 and 13 are cross-sectional views of the sleeve member illustrating different sensor systems/arrangements for determining depth of a drilled hole.
Figure 13:
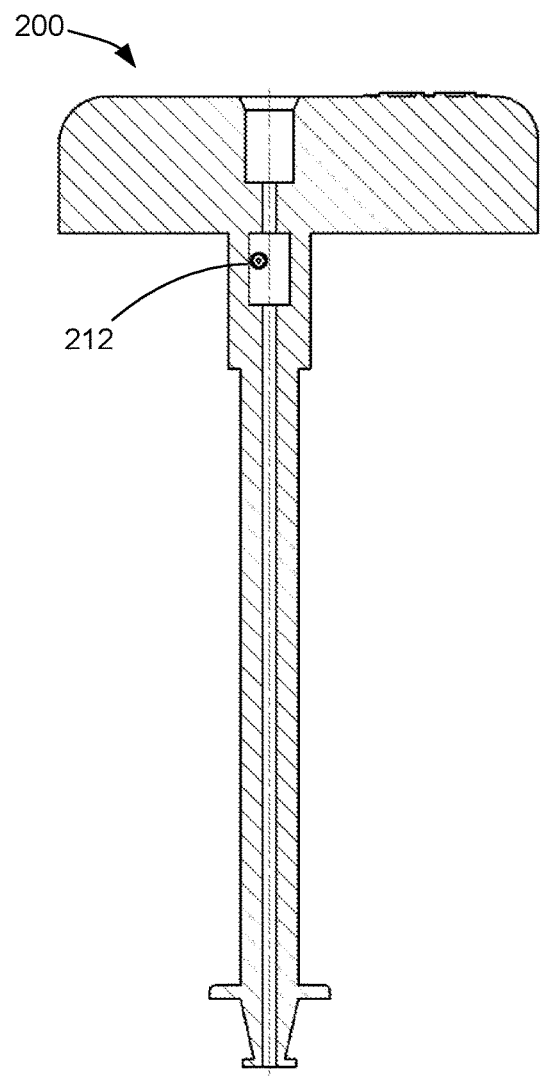

FIGS. 12 and 13 are cross-sectional views of the sleeve member 200 illustrating different sensor systems/arrangements for determining depth of a drilled hole based on movement of the probe 300. In some embodiments, the sensor system may include a potentiometer 210 arrangement (FIG. 12). In some embodiments, as shown in FIG. 13, the sensor system for determining depth may include a worm gear measurement system, wherein the sleeve member 200 may include a pinion gear 212 and the probe may have a corresponding worm gear configuration on its exterior surface. Yet still, in some embodiments, the sensor system may include a laser diode configured to read or otherwise sense machine-readable markings on the probe to determine distance traveled when determining/calculating depth of the drilled hole.

It should be noted that the surgical instrument may include logic or allow for adjustment to the sensing capabilities so as to program the sensor to account for other variables when sensing the depth of the hole. For example, in some embodiments, certain procedures require fixing a plate or implant to the bone via screws. Accordingly, the screw length must not only be sufficient to fill the hole but also long enough to account for the thickness of a plate or implant through which it passes when engaging the hole. Accordingly, in some embodiments, the sensor may be programmed so as to account for the thickness of the plate or implant and will further include that thickness in the electronic signal produced, such that the electronic signal is indicative of the total depth that a corresponding screw length will need to cover, including the depth of the hole in the bone in addition to the thickness of the plate or implant through which the screw will pass through and the screw head will engage.

Accordingly, the digital sensing of the hole depth provides a much more accurate measurement than conventional analog depth gauges and also requiring very little, if any, input or interpretation from the surgeon. Accordingly, by providing a much more accurate measurement of a hole depth, the surgeon is able to select the correct length screw for any given hole so as to improve the chances of a successful surgery.

In some embodiments, the surgical instrument may further include a display provided on the sleeve member 200, for example, and may be configured to visually provide a digital readout of a depth measurement of the hole based on the electronic signal from the sensor. In other embodiments, the surgical depth instrument may be configured to wirelessly communicate and exchange data with a separate display or computing device, such as, for example, a monitor or panel display, a PC, a notebook, a tablet computer, a smartphone, or other wireless computing device.

Upon receiving the electronic signal from the sensor, the separate display or computing device may be configured to visually provide the depth measurement of the hole based on the electronic signal from the sensor. Furthermore, in some embodiments, the computing device may include a specific software application that may be directed to maintaining a record of the hole measurements and/or provide an interactive user interface in which multiple holes can be mapped to a particular plate or implant and the depth of each hole (including the thickness of the plate or implant) can be included and stored for records.

FIGS. 14A-14H illustrate a series of steps for performing a procedure of deploying the hook member 102 of the guidewire 100 and subsequently obtaining a depth measurement using the surgical depth instrument, specifically the sleeve member 200 and probe 300 consistent with the present disclosure. As shown in FIG. 14A, a procedure may begin in which the surgeon, or other medical professional, begins to advance the guidewire 100, specifically the hook member 102, into a drilled hole in a bone. The hook member 102 is in the delivery configuration, and due to its compact size while in the delivery configuration, the hook member 102 may be freely positioned within and move through the drilled hole. In the figures, the hole is drilled entirely through the bone (i.e., bicortical drill hole), and thus the surgeon advances the hook member 102 entirely through the hole, as shown in FIG. 14B.

Upon reaching the desired position, the surgeon then actively controls transitioning of the hook member from the delivery configuration to the deployed configuration, as shown in FIG. 14C. In this instance, the surgeon would like to obtain the depth of the hole for the purpose of selecting the correct length of screw to use for the bicortical drill hole. Accordingly, upon transitioning the hook member to the deployed configuration, in which the expanded diameter is much greater than the drilled hole diameter and opening, and the surgeon pulls back on the guidewire 100 until the expanded hook member 102 securely engages the exterior surface of the bone adjacent to the drilled hole, as shown in FIG. 14D. Due to the resilient nature of the material of the struts, the hook member 102 may essentially flatten against the surface of the bone in response to the surgeon pulling back on the guidewire 100, and the flattening may enhance tactile feel, providing the surgeon with an indication that the hook member 102 is sufficiently anchored.

At this point, with the guidewire secured 100 in position, the surgeon can simply slide the sleeve member 200 over the guidewire 100 and further assembly the probe 300 with the sleeve member 200, as shown in FIG. 14E. In order to begin the depth measurement of the hole via the probe 300, the surgeon may first advance the sleeve member 200, while mounted to the guidewire 100, towards the opening of the hole until the distal end 204 of the sleeve member 200 engages at least the opening of a drilled hole, at which point, the flanged member 205 is configured to engage the exterior surface of the bone along a periphery of the hole opening, as shown in FIG. 14F. The distal end 204 of the sleeve member 200 establishes engagement and maintains the sleeve member 200 in a stabilized position, at which point, the probe 300 can be used for measuring the depth of the hole. In particular, as shown in FIG. 14G, the surgeon advances the probe 300 within the hole until it reaches the anchored hook member 102, which serves as a stopping point for the probe 300 and thus provides a datum from which the depth of the hole can be determined. Upon the distal tip 306 of the probe 300 engaging the hook member 102, shown in FIG. 14H, the measurement of the depth of the hole is now complete, in that the sensor has determined the distance traveled by the probe 300 and thus is able to calculate the corresponding depth of the hole.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

What is claimed is:

1. A method for the measurement of a hole formed in a bone, the method comprising:
   introducing to a hole formed in a bone a guidewire comprising a deployable hook member configured to transition between a delivery configuration, in which the hook member has a first diameter and is configured to be positioned within and move through the hole, and a deployed configuration, in which the hook member has a second diameter greater than the first diameter;
   moving the hook member through the hole;
   positioning the hook member within the hole;
   transitioning the hook member to the deployed configuration thereby anchoring the hook member at a position relative to the hole;
   introducing to the hole formed in the bone a surgical depth instrument comprising a sleeve member and a probe member cooperatively coupled thereto, the sleeve member having a distal end, a proximal end, and a bore extending from the distal end to the proximal end, wherein the bore is configured to receive the guidewire therethrough, wherein the distal end of the sleeve member is configured to engage an opening of the hole upon movement of the sleeve member towards the hole, and wherein the distal end of the sleeve member comprises one or more protrusions configured to establish purchase with a portion of the interior surface of the hole upon rotation of the sleeve member, wherein the sleeve member and probe member are each configured to move relative to the hook member along as axis of the guidewire, wherein the surgical depth instrument is configured to obtain at least one measurement of the hole based, at least in part, on engagement between a distal tip of the probe member of the surgical depth instrument and the hook member when the hook member is in the deployed configuration;
   receiving the guidewire in the bore of the sleeve member thereby slidably mounting the sleeve member to the guidewire;
   moving the sleeve member and the probe member relative to the hook member along an axis of the guidewire towards the hole;
   engaging an opening of the hole with the sleeve member;
   rotating the sleeve member thereby establishing purchase with a portion of the interior surface of the hole; and
   obtaining at least one measurement of the hole based, at least in part, on engagement between the distal tip of the probe member and the hook member.

2. The method of claim 1, wherein the probe member comprises an elongate body and the bore is configured to receive at least a portion of the elongate body of the probe member and the distal tip of the probe member therethrough, and the method comprises receiving at least a portion of the elongate body of the probe member and the distal tip of the probe member therethrough prior to moving the sleeve member and the probe member relative to the hook member along an axis of the guidewire towards the hole.

3. The method of claim 2, wherein the distal tip of the probe member and a portion of the elongate body extends from the distal end of the sleeve member after being received by the bore.

4. The method of claim 1, wherein the probe member comprises a hollow elongate body configured to receive the guidewire therethrough to thereby slidably mount the probe member to the guidewire, and wherein the method comprises receiving the guidewire in the elongate body of the sleeve member thereby slidably mounting the sleeve member to the guidewire, prior to moving the sleeve member and the probe member relative to the hook member along an axis of the guidewire towards the hole.

5. The method of claim 1, wherein the surgical depth instrument further comprises a sensor configured to generate an electronic signal indicative of a depth of at least the hole, wherein the electronic signal varies in relation to a distance traveled by the probe member relative to the sleeve member, and wherein the method comprises generating an electronic signal indicative of a depth of at least the hole.

6. The method of claim 5, wherein the sensor is an electrical resistance-based sensor.

7. The method of claim 6, wherein the sensor comprises a potentiometer.

8. The method of claim 5, wherein the sensor is configured to generate an electronic signal based on a worm gear assembly.

9. The method of claim 8, wherein the worm gear assembly comprises a pinion gear and the probe member comprises a corresponding worm gear arrangement on a surface thereof.

10. The method of claim 5, further comprising a display on the sleeve member configured to visually provide a digital readout of a depth measurement of the hole based on the electronic signal from the sensor, and wherein the method comprises visually providing a digital readout of a depth measurement of the hole based on the electronic signal from the sensor.

11. The method of claim 10, wherein the display is a liquid crystal display or an LED display.

12. The method of claim 1, wherein after being transitioned into the deployed configuration, the hook member provides a datum from which the at least one measurement of the hole is based.

13. The method of claim 1, wherein the hook member comprises a plurality of struts, each having a distal end fixed to a common distal-most end of the guidewire and a proximal end fixed to a common portion of the guidewire positioned a distance from the distal-most end of the guidewire.

14. The method of claim 13, wherein the guidewire further comprises a pull-wire coupled to the distal-most end of the guidewire.

15. The method of claim 14, wherein the hook member is configured to transition from the delivery configuration to the deployed configuration upon application of a pulling force to the pull-wire, and wherein transitioning the hook member to the deployed configuration comprises applying pulling force to the pull-wire.

16. The method of claim 15, wherein the method comprises transitioning the hook member to the delivery configuration and removing the guidewire from the hole after obtaining at the least one measurement of the hole.

17. The method of claim 16, wherein the hook member is configured to transition from the deployed configuration to the delivery configuration upon removal of the pulling force from the pull-wire, and wherein transitioning the hook member to the delivery configuration comprises removal of the pulling force from the pull-wire.

* * * * *